United States Patent
Wallace et al.

[11] Patent Number: 5,649,949
[45] Date of Patent: Jul. 22, 1997

[54] VARIABLE CROSS-SECTION CONICAL VASOOCCLUSIVE COILS

[75] Inventors: Michael P. Wallace, Pleasanton; Francisco S. Villar, Newark; Christopher G. M. Ken, San Mateo; David A. Gyorke, El Cerrito, all of Calif.; Timothy S. Winkle, Gilbert, Ariz.

[73] Assignee: Target Therapeutics, Inc., Fremont, Calif.

[21] Appl. No.: 625,805

[22] Filed: Mar. 28, 1996

Related U.S. Application Data

[63] Continuation of Ser. No. 615,130, Mar. 14, 1996.

[51] Int. Cl.⁶ ................................................. A61B 17/12
[52] U.S. Cl. .................... 606/191; 606/198; 600/200; 604/104; 623/1; 623/11
[58] Field of Search ............................ 606/194, 198, 606/200, 191; 604/104; 623/1, 11, 12

[56] References Cited

U.S. PATENT DOCUMENTS

| | | |
|---|---|---|
| 4,619,246 | 10/1986 | Molgaard-Nielsen et al. |
| 4,638,803 | 1/1987 | Rand |
| 4,994,069 | 2/1991 | Ritchart et al. |
| 5,122,136 | 6/1992 | Guglielmi et al. |
| 5,217,484 | 6/1993 | Marks |
| 5,234,437 | 8/1993 | Sepetka |
| 5,250,071 | 10/1993 | Palermo |
| 5,261,916 | 11/1993 | Engelson |
| 5,304,195 | 4/1994 | Twyford, Jr. et al. |
| 5,312,415 | 5/1994 | Palermo |
| 5,334,210 | 8/1994 | Gianturco |
| 5,350,397 | 9/1994 | Palermo et al. |
| 5,354,295 | 10/1994 | Guglielmi et al. |
| 5,413,586 | 5/1995 | Dibie et al. |
| 5,417,708 | 5/1995 | Hall et al. |
| 5,423,777 | 6/1995 | Tajiri et al. |
| 5,443,478 | 8/1995 | Purdy |

FOREIGN PATENT DOCUMENTS

| | | |
|---|---|---|
| 4-312454 | 11/1992 | Japan |
| WO92/14408 | 9/1992 | WIPO |
| WO95/25480 | 9/1995 | WIPO |

*Primary Examiner*—Michael Buiz
*Assistant Examiner*—Nancy Mulcare
*Attorney, Agent, or Firm*—Morrison & Foerster

[57] ABSTRACT

This is an implantable vasoocclusive device. It is constructed of a primary helically wound coil, which primary coil is further wound into secondary shapes which are at least partially substantially conical. Other portions of the secondary shape may have sections of constant diameter or of other conical shapes. The primary coil may be made in such a way that it has regions of differing flexibility. Fibrous materials may be placed on the coils in tufted, streamer, or woven configurations so to increase the thrombogenicity of the overall assembled device.

28 Claims, 8 Drawing Sheets

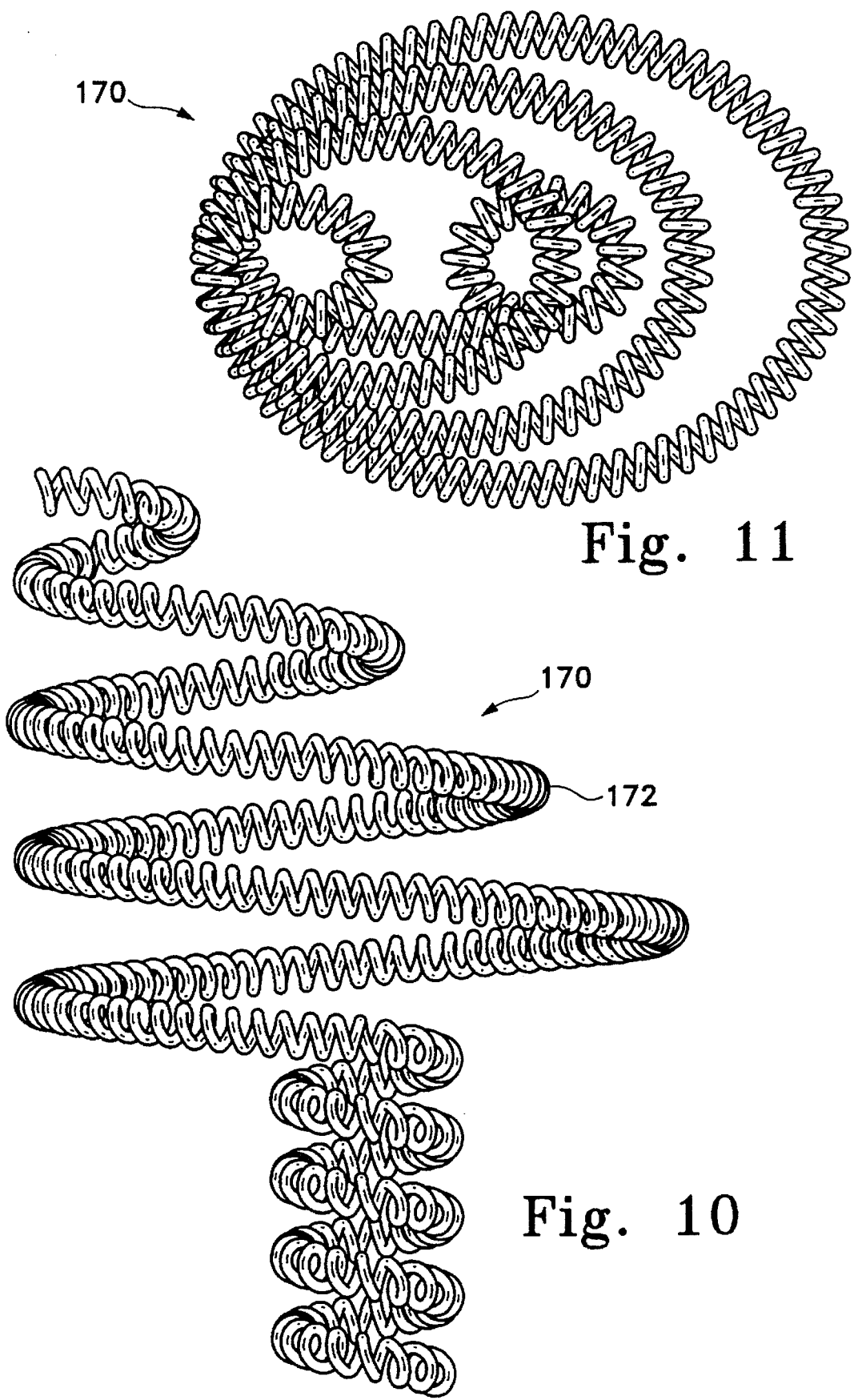

VARIABLE CROSS-SECTION CONICAL VASOOCCLUSIVE COILS

RELATED APPLICATIONS

This application is a continuation of U.S. Ser. No. 08/615,130 filed Mar. 14, 1996 titled VARIABLE CROSS-SECTION CONICAL VASOOCLUSIVE COILS (Attorney Docket No. 290252015300).

FIELD OF THE INVENTION

This invention is an implantable vasoocclusive device. It is constructed of a primary helically wound coil, which primary coil is further wound into a secondary shape which secondary shape is at least partially substantially conical. Other portions of the secondary shape may have regions of constant diameter or of other conical shapes. The primary coil may be made in such a way that it has regions of differing flexibility. Fibrous materials may be placed on the coils in tufted, streamer, or woven configurations so to increase the thrombogenicity of the overall assembled device.

BACKGROUND OF THE INVENTION

There are a number of useful procedures for introducing implants into open regions of the human body, e.g., aneurysms, for the purpose of closing that region. Various interventional procedures using catheters deliver occlusive wire coils, detachable balloons, or coagulative or glue-like substances into a variety of body regions. For instance, it is common to control internal bleeding or to fill aneurysms with such devices or materials so to limit the flow of blood or to lessen contact of the aneurysm wall to the blood pressure. It is also common to use such procedures in restricting the flow of blood to tumors.

Delivery of vasoocclusive coils through various catheter delivery systems is a complicated task, particularly when the coil has both a linear primary shape and a convoluted secondary shape once it is ejected from the tip of the catheter. Vasoocclusive coils having secondary shapes are used for a variety of reasons. Such coils present multiple surfaces to the blood so to cause the formation of embolus. Further, a coil having a properly shaped secondary configuration will engage the wall of the vessel and anchor the coil in place. Long coils assuming a random configuration once ejected from the catheter are also known. Although these long, randomly oriented secondary shape coils are quite good at presenting fresh thrombogenic surfaces and hence easily form thrombi, there is a trade-off to be accounted for. Should the coil be of the wrong size or be mal-placed, such long coils are difficult to reposition or to remove. Consequently, it is sometimes desirable to use a coil having a smaller amount of metal but with a more calculated shape so to allow easy removal or re-placement while still readily forming thrombus. Furthermore, shorter coils exhibit less friction when being pushed through a catheter lumen. Such improved friction characteristics allows placement of coils in more distal vasculature, such as found in the brain, than other longer, higher friction devices. The devices described herein are suitable for forming thrombus and yet may be readily removed or repositioned as needed.

There are a number of known vasoocclusive devices having secondary shapes.

One such device may be found in U.S. Pat. No. 4,994,069, to Ritchart et al. Ritchart et al. describes a variety of regular and random secondary shapes for vasoocclusive devices which may be ejected from the distal tip of an intravascular catheter. A conical device is shown in the FIG. 5.

U.S. Pat. Nos. 5,122,136 and 5,354,295, both to Guglielmi and Sepetka, describe vasoocclusive coils having secondary forms which are "cylindrical or conical" at column 6, lines 23–34. These coils are used to provide support for emboli formed in various vascular cavities of the body.

Another conical vasoocclusive coil is shown in WO95/25480, to Tekulve.

U.S. Pat. No. 5,334,210, to Gianturco, describes a vascular occlusion assembly. The assembly is made up of a foldable material occlusion bag having an expanded diamond shape and an elongated flexible filler member which is inserted into the internal cavity of the occlusion bag. The filler member is apparently typically a helically wound coil which is introduced into and ultimately is designed to fill the occlusion bag.

None of the prior art discussed above discloses any of the variations of the inventive vasoocclusive device described below.

SUMMARY OF THE INVENTION

This invention is an implantable vasoocclusive device. In general, it is a vasoocclusive helically wound coil which is provided with a secondary shape. Such secondary shape, when viewed along its longitudinal axis, has at least a portion which varies in effective diameter. In the most basic of the variations made according to this invention, this variation in effective diameter of the secondary shape results in a simple conical shaped device. In more complicated variations of the invention, certain portions of the secondary form of the coil may have short regions which are somewhat more tubular in configuration than their adjacent regions. The secondary shape may have regions in which the primary coil has regions which are generally straight and yet form abstract triangular, square, or other polygonal shapes when released into the secondary shape.

The section of the vasoocclusive device having a varying effective diameter may be assembled with an adjunct section of the device having constant diameter.

The primary shape of the device is typically a helical coil. The stiffness of the primary helical coil making up the device may be also varied in a variety of ways. For instance, the wire forming the vasoocclusive device itself may have regions of higher and lower flexibility, perhaps caused by a change in local wire diameter. The primary winding diameter may be varied to change the local flexibility of the primary coil as well. Other variations such as changing the pitch of the winding may also be used.

The devices may be used with or without the presence of ancillary fibers such as Dacron to enhance the device's overall thrombogenicity.

In general, the device is used in the human vasculature to form emboli. Such emboli may be used to close the feed artery to a tumor, fill an aneurysm, or close a vessel to a vascular accident such as a stroke. The device may also be used to close other lumen or openings in the human body, such as fallopian tubes, if the need arises.

The device is typically deployed from a catheter which has been placed there using known techniques.

BRIEF DESCRIPTION OF THE DRAWINGS

FIGS. 10 and 11 show, respectively, side and top views of an eliptically shaped variation of the invention shown in FIGS. 8 and 9.

DESCRIPTION OF THE INVENTION

This invention is a helically wound vasoocclusive coil which may be introduced into the human body, particularly into the human vasculature, using a catheter. The inventive device is of a type which has a primary coil. The helically wound primary coil is then wound into a secondary shape having at least some aspect of a conical form.

Figure 1:
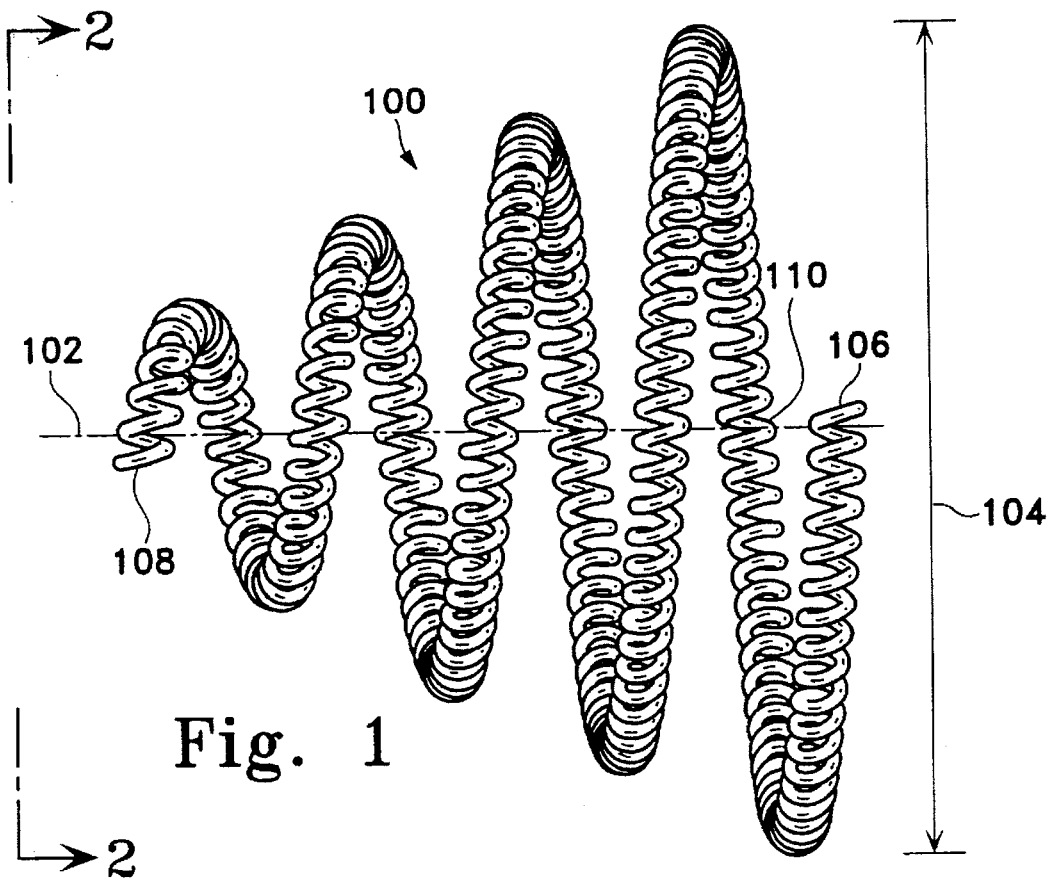
FIGS. 1 and 2 show, respectively, side and top views of a spirally shaped vasoocclusive device made according to the invention.
Figure 2:
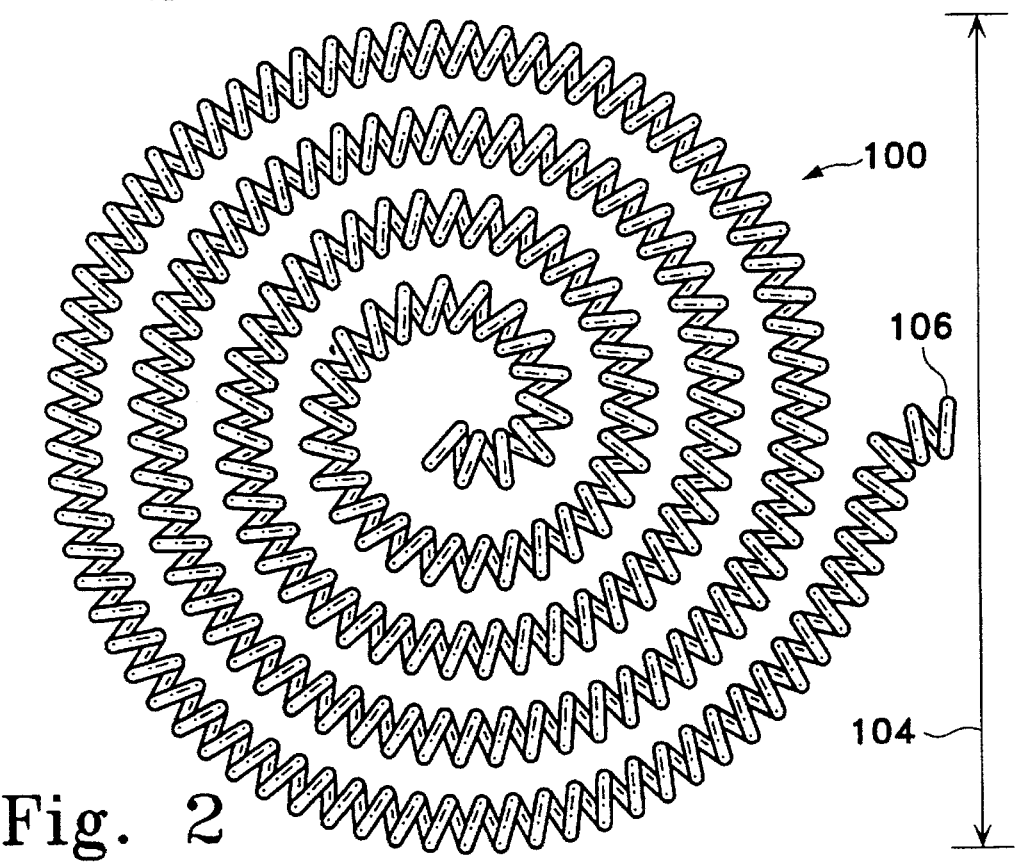

FIG. 1 shows a basic variation of the inventive device having the general secondary form of a spiral. This variation (100) has a conical axis (102) and an outer radius (104). As noted above, this variation of the invention (100) has a generally conical shape and forms a conical envelope. It is produced from a wire thread which is first wound helically into a primary helical spring form and once, so wound, is then wound into a secondary form such as found in FIGS. 1 or 2. FIG. 2 shows a view of vasoocclusive coil (100) along the axis (102). Outer diameter (104) is generally selected so that, when unconstrained, it is slightly larger than the vessel into which it is placed. This allows the vasoocclusive device (100) to engage the inner lumen of the selected vessel in such a way that axis (102) is generally aligned with the axis of blood vessel tureen. Although it is not critical to this invention, the vasoocclusive device having the shape found in FIGS. 1 and 2 may include a small pigtail (106) which further is able to enhance the ability of the device (100) to engage the interior of the vessel wall.

Again, although not critical to this invention, it is often desirable that the length of axis (102) from the apex of the coil (108) to the base of the coil (110) is less than or about the same as the size of the outer diameter (104).

Central to the embodiment shown in FIGS. 1 and 2 is the use of a primary coil having a variety of regions along its axis with differing flexibilities. The physical parameters of the primary coil are varied in such a way that the flexibility of the primary coil is also varied. For instance, in FIG. 3, the diameter of the wire (112) and the diameter (114) of the primary coil (116) are maintained at generally constant values throughout the region observed. The pitch or spacing between turns is seen to vary substantially in the region shown in FIG. 3.

Figure 4:
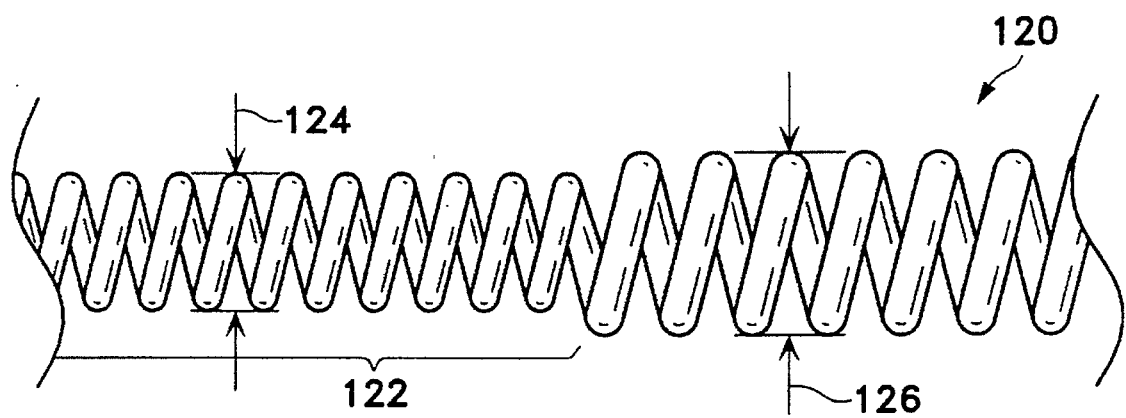

The portion of the primary coil (120) shown in FIG. 4 includes a portion (122) of a primary coil (120) having both a small primary diameter (124) and a larger primary diameter (126). The flexibility of one end of coil section (120) is different than the flexibility at the other end of coil section (120).

Figure 5:
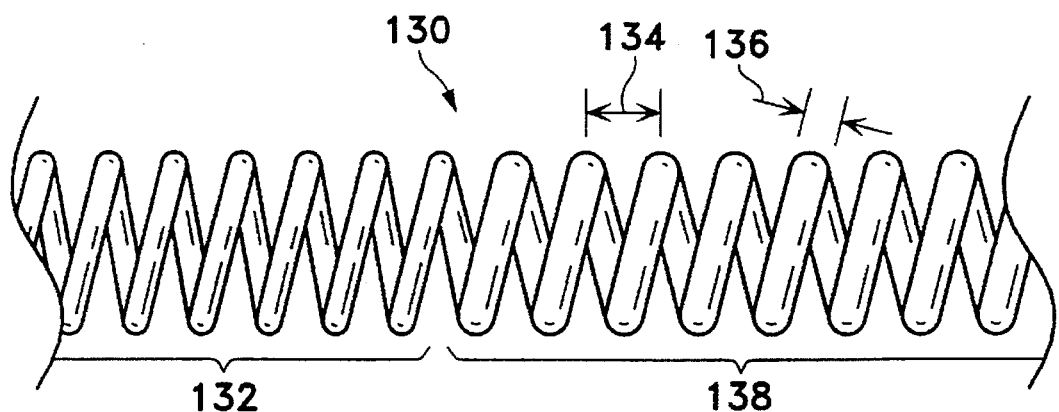

Similarly, in FIG. 5, is shown a coil section (130) having a region (132) in which both the space between windings of the helical coil is small and the overall diameter of the wire in that section is small, in each case, compared to the larger spacing between coil turns (134) and the diameter of the wire (136) found in coil section (138). In this way, the respective flexibility of the ends of the coil section (130) are quite different.

Figure 3:
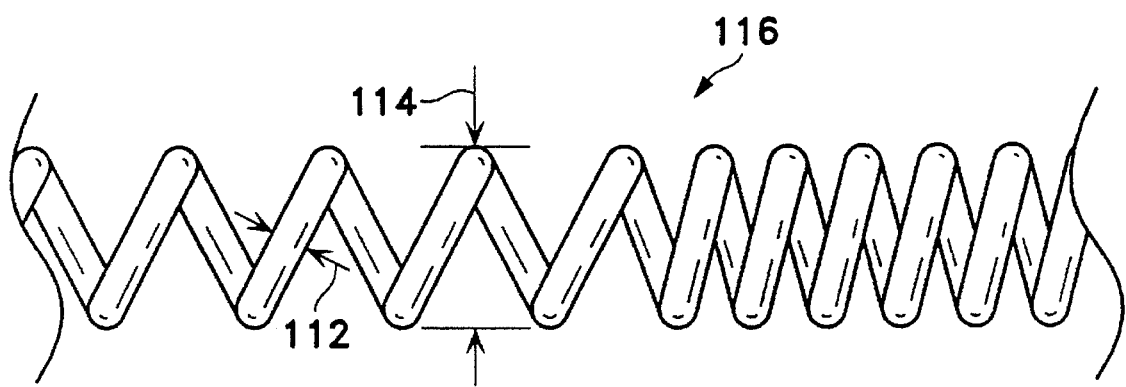
FIGS. 3, 4, and 5 depict in magnified side view, the primary shapes of helical coils suitable for use in the secondary forms of the inventive vasoocclusive device.

The variations of coil stiffness as shown in FIGS. 3, 4, and 5 may be used in producing the coils found in FIGS. 1 and 2 and optionally in producing the other vasoocclusive coils made according to this invention. Other methods of changing the flexibility of the wire, e.g., by changing composition of the wire along its axis or by annealing regions of the wire are also included.

The materials making up the vasoocclusive devices found in FIGS. 1–5 and those which are described below are typically metallic. These metallic materials are typically selected from platinum, gold, rhodium, rhenium, palladium, tungsten, and the like, as well as alloys of these metals. Especially preferred for these vasoocclusive devices are alloys of platinum and up to about 15% tungsten. These metals and alloys have significant radioopacity and their alloys may be tailored to accomplish an appropriate flexibility. These materials are also largely biologically compatible.

The material making up the vasoocclusive coils may be of other suitable biocompatible materials, (e.g., polymers), composites of metals or alloys and polymers, etc. It is only necessary that the device hold its shape upon introduction into the vasoocclusive region and that it be significantly biocompatible. Polymeric wire materials are often mixed with a radioopaque material, such as barium sulfate, bismuth trioxide, bismuth carbonate, powdered tungsten, powdered tantalum, or the like, to promote their passive ability to be visualized using fluoroscopy.

The diameter of the wire typically used in this invention will typically be in the range of 0.0005 and 0.008 inches. Larger diameter wire (e.g., 0.003 to 0.008 inches) may be desired for very specific indications where occlusion is needed at a high volume flow rate site. Such might include repair of an infant's Vein of Galen and treatment of arteriovenous malformations (AVM's). Larger diameter wire would be chosen because of its springiness. Materials with higher innate springiness, e.g., platinum alloys with high tungsten content, would also be suitable for such high flow regions.

The primary coil diameter (114 in FIG. 3 and 124 and 126 in FIG. 4) will nominally be in the range of 0.008 and 0.075 inches. For most neurovascular indications, a range of 0.010 and 0.018 inches is acceptable. For many peripheral applications or neurological applications where large vessel abnormalities are found(e.g., Vein of Galen malformations or dural fistulae), the primary coil diameter is usually less than about 0.060 inches, preferably 0.018 to 0.038 inches. The axial length of the primary shape will usually fall in the range of 0.5 to 100 centimeters, more usually 2 to 40 centimeters. Depending upon usage and wire diameter, the coil may well have 10 to 200 turns per centimeter. All of the dimensions noted here are provided only as guidelines and are not critical to the statement of the invention. However, only dimensions which are suitable for occluding sites within the human body are included within the scope of this invention.

In the variation of the vasoocclusive coil shown in FIGS. 1 and 2, it is desirable to utilize the primary coil variations such as are shown in FIGS. 2, 3, and 4 in such a way that at least a major portion of the first or outer mm of the secondary shape of FIGS. 1 and 2 is stiffer than the remainder of the secondary turns. This obviously provides a secondary shape in which the outer region which contacts the vessel lumen is more able to engage the wall of the vessel lumen and maintain both the placement and orientation of the device once it is situated within the site to be occluded. Although it is desirable to limit the amount of coil having a region of lower flexibility, the number of rams need not be so limited. It is desirable, as shown in FIGS. 1 and 2, that up to seven or eight rams of secondary shape be attained between the apex and the large end. Any or all of these turns may be relatively stiffer but, as noted above, it is preferred that only the outer turn or largest turn be of enhanced stiffness.

Figure 6:
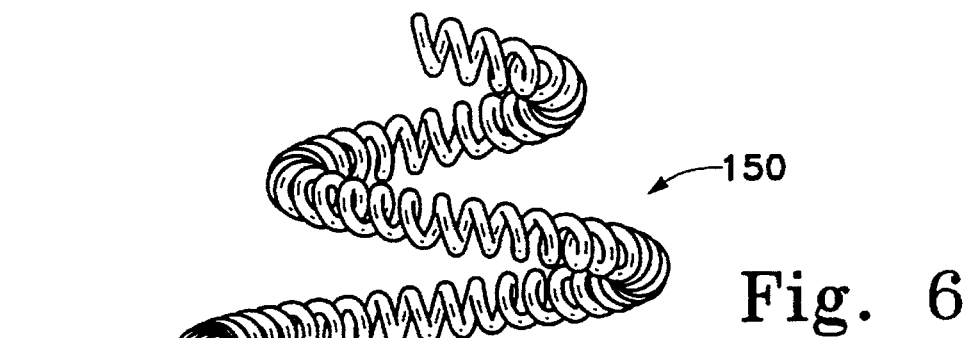
FIGS. 6 and 7 show, respectively, side and top views of a conical vasoocclusive device having an interior filler coil.
Figure 7:
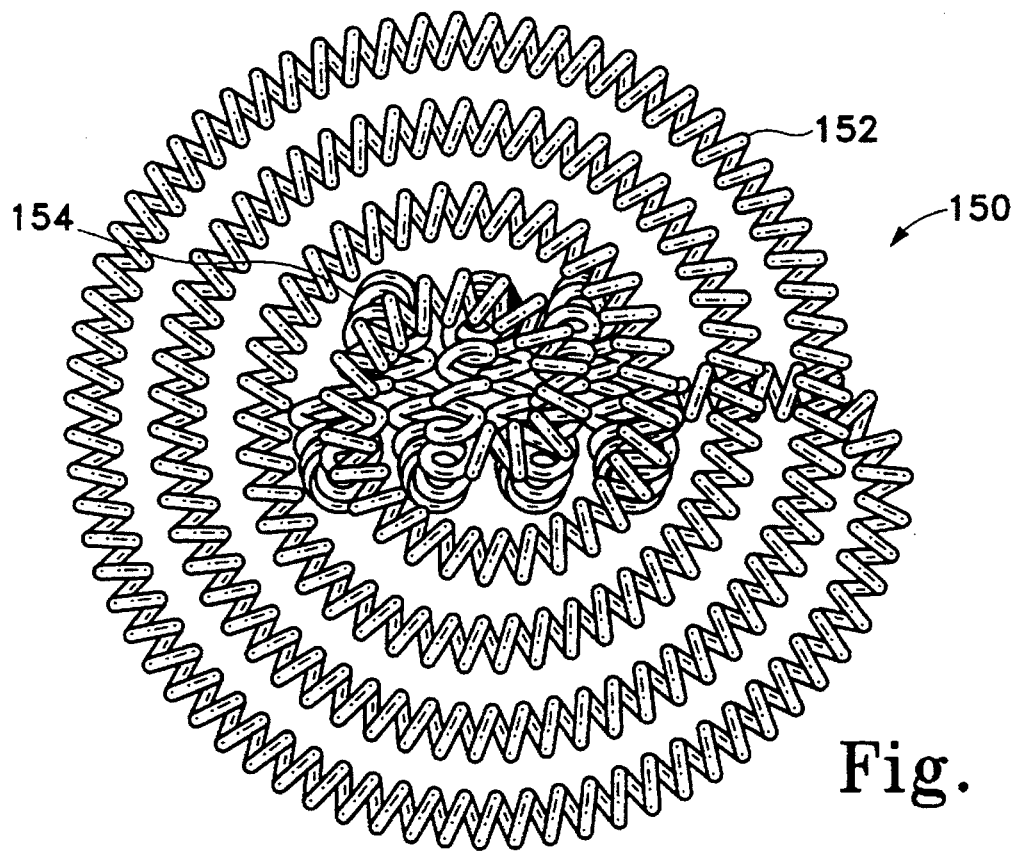

FIGS. 6 and 7 show, respectively, side views and top views of another variation of the invention. The variation (150) shown in FIGS. 6 and 7 comprises two sections: a conical section (152) and a filler section (154). The conical section is of the same, generally a spiraling, circular form of decreasing (or increasing) radius secondary coils. The filler section (154) extends into the conical region formed by the interior of the conical section (152) It is a generally constant diameter section used to in-fill the conical section (152). FIGS. 6 and 7 show the in-filling section (154) to be of a constant diameter and have an axis which is approximately perpendicular to the axis of the conical section (152).

The size of filler section (154) is not particularly critical. It is placed in the open region within conical section (152) merely to provide extra surfaces with which to begin the formation of embolus after deployment of vasoocclusive device (150). The length of filler section (154) may be as much as 50% of the overall diameter of the large end of the conical section (152). Alternatively, the shape of filler coil (154) need not be of constant radius but may be of some other form suitable for this device. For instance, the axis of filler section (154) may be the same as or parallel to the axis of conical section (152).

Figures 8, 9:
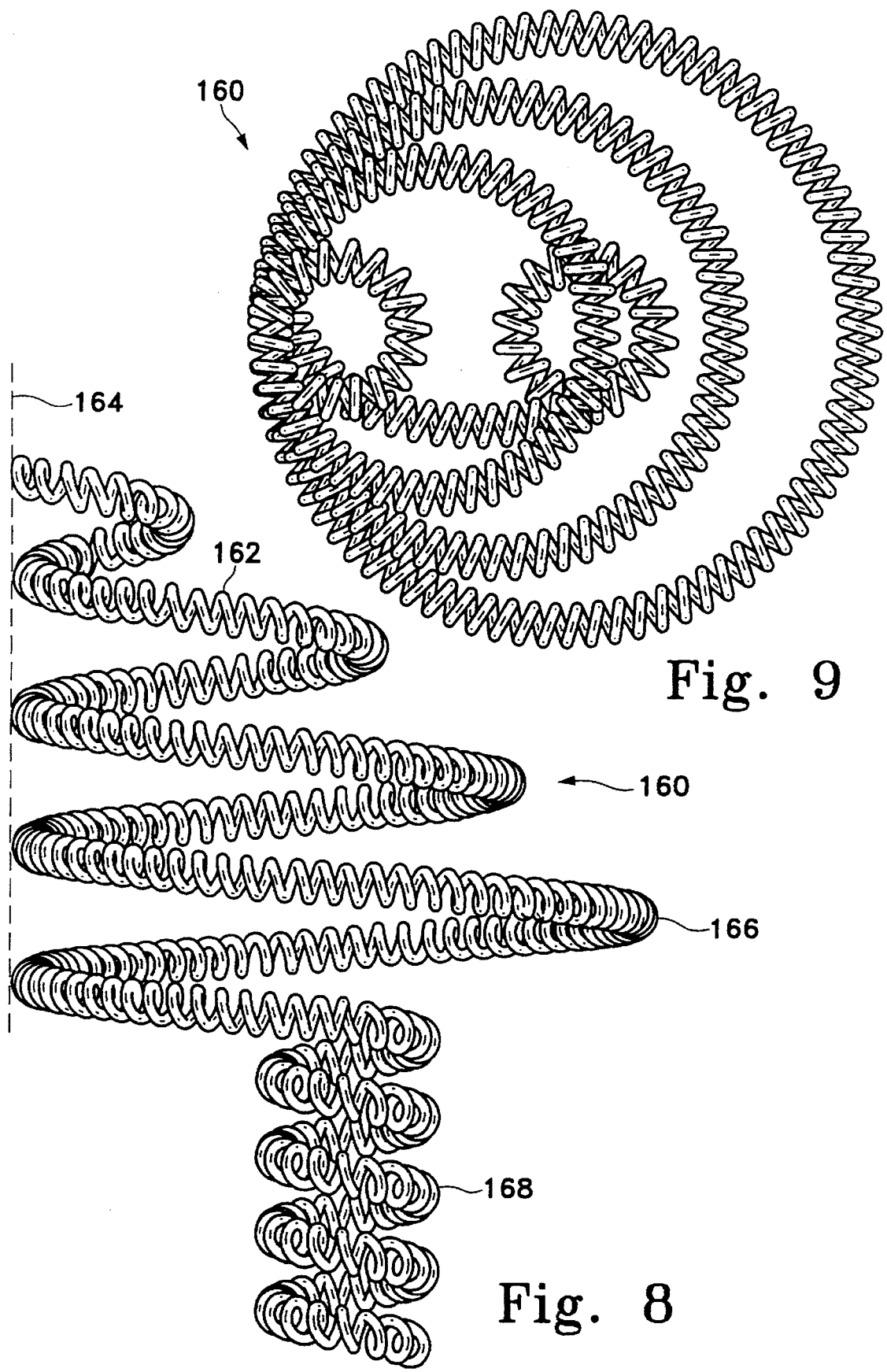
FIGS. 8 and 9 show, respectively, side and top views of a skewed vasoocclusive device having a tapered portion and a portion with a constant diameter.

FIGS. 8 and 9 show, respectively, a side view and a top view of a variation of the device shown in FIGS. 6 and 7. In this variation, (160), the conical section (162) is skewed so that the axis (164) is generally tangent to the turns of the coil and generally perpendicular to the large coiled end (166). Additionally, the filler section (168) extends from the big turn (166) of the conical section (162) in such as way that it is more of a "pigtail" extending away from the opening formed by the conical section (162). Filler section (168) may extend upwardly into the conical section (162) opening, as well. In this instance, the filler section (168) axis is generally parallel to axis (164).

It may be seen from FIG. 9 that this variation (160) is generally round.

FIGS. 10 and 11 show a variation of the device shown in FIGS. 8 and 9. The principal difference is simply that the conical section (172) is elliptical in form.

Figure 12:
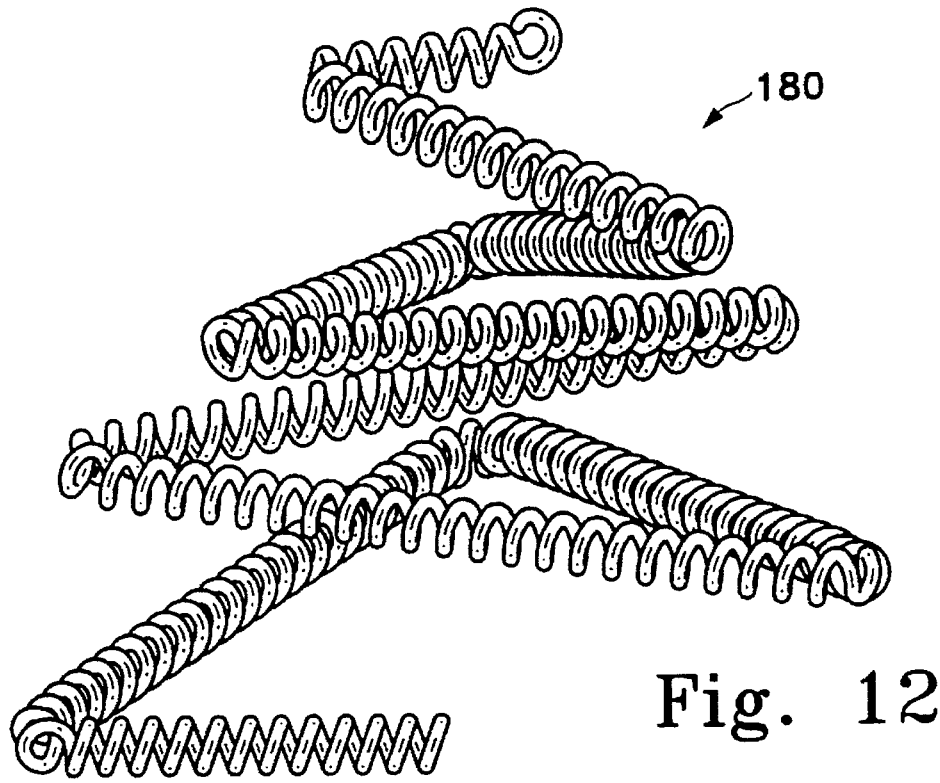
FIGS. 12 and 13 show, respectively, side and top views of a variation of the invention having a twisted triangular form.
Figure 13:
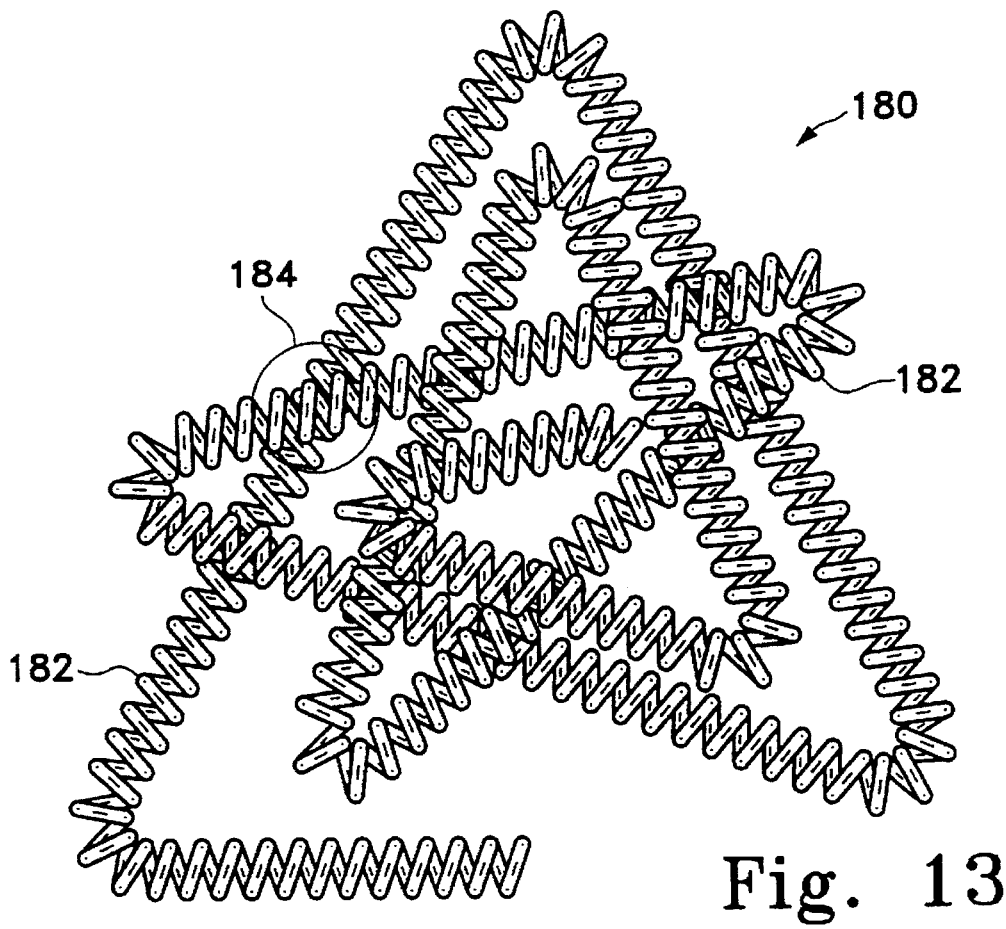

FIGS. 12 and 13 show, respectively, side and top views of another variation (180) of the inventive occlusive device in which a generally or abstractly triangular shape is applied to the secondary form. In particular, this is shown in the top view in FIG. 13. In this variation, the conical section is made up of a number of approximately straight sections which, when viewed along the axis of the cone, form generally a triangular shape. The device may be wound in such a way that the straight sections (182) may be aligned to be parallel to another straight section in an adjacent turn. This variation is not shown in FIG. 13. The variation of FIG. 13 shows secondary coil turns having straight regions (182) which meet other layers at nodes (184). These nodes (184) will, in certain circumstances, provide a more determinate structure to the overall coil assembly (180) after deployment.

Figure 14:
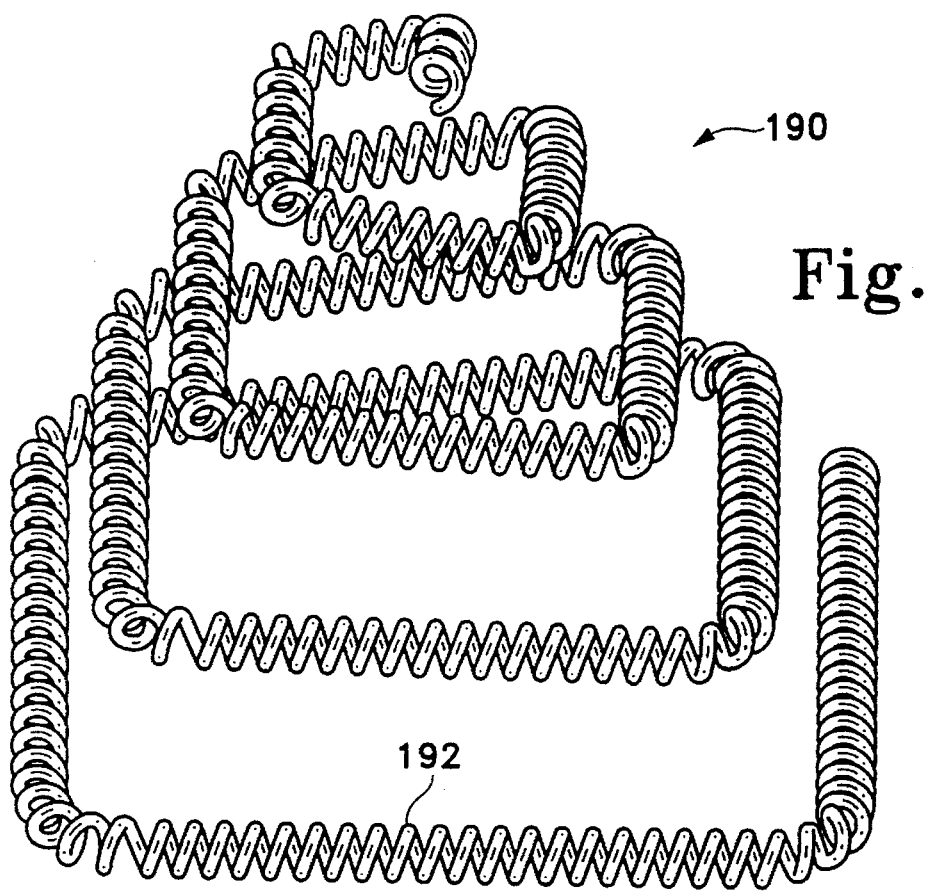
FIGS. 14 and 15, show, respectively, side and top views of a pyramidal variation of the device made according to the invention.
Figure 15:
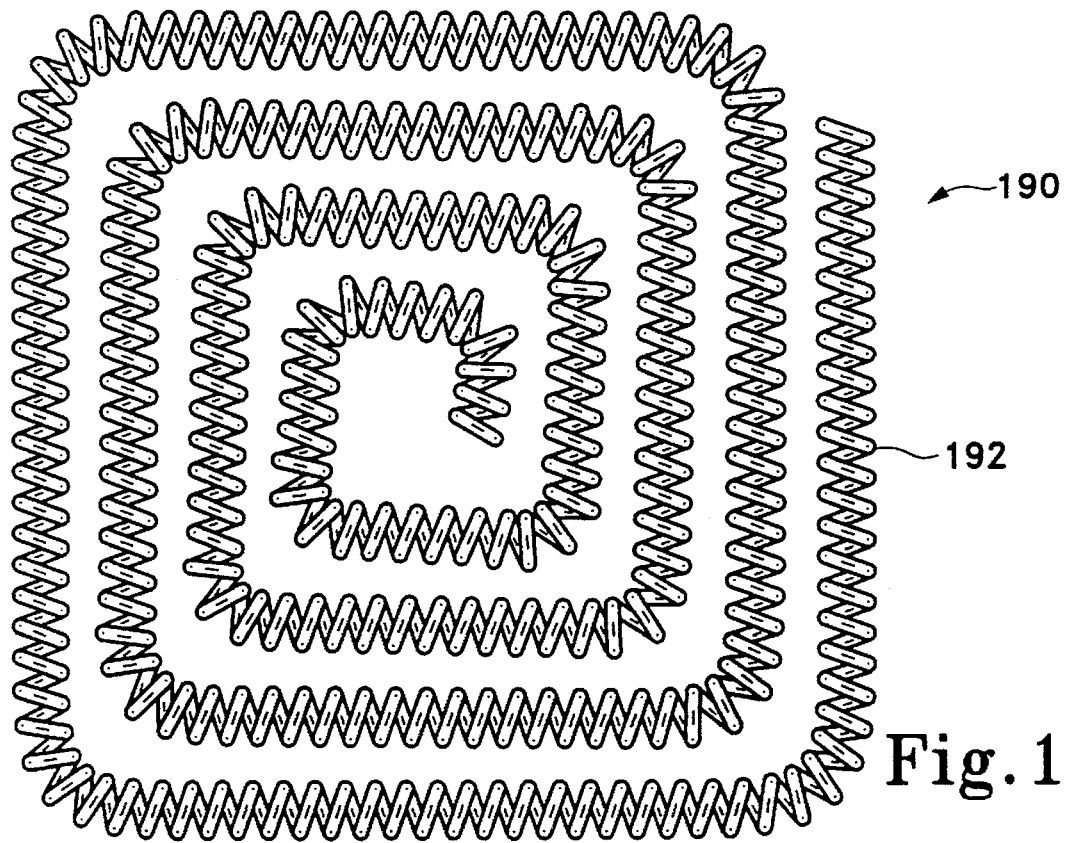

FIGS. 14 and 15 show, respectively, side and top views of another polygonal conical coil assembly in which the straight regions (192) generally form a smoothed square or rectangle. Again, the device has a conical aspect to it which, because of the reasonably straight sides (192) results in a rounded pyramid upon deployment of the device.

Each of the devices shown in the above figures may be constructed with a filler section either as shown in FIGS. 6 and 7 or in a pigtail configuration such as is shown in FIGS. 8–11. Further, each of the devices shown in FIGS. 6–15 may be made employing variable stiffness such as may be achieved by varying a physical parameter of the primary coil as indicated in FIGS. 3–5.

Figure 16A:
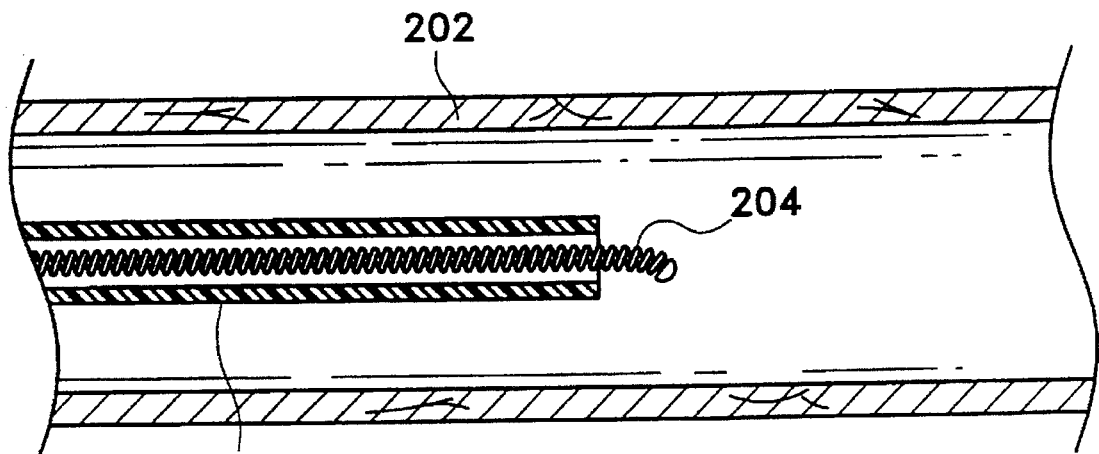
FIGS. 16A–16C show a procedure for deploying the inventive device.
Figure 16B:
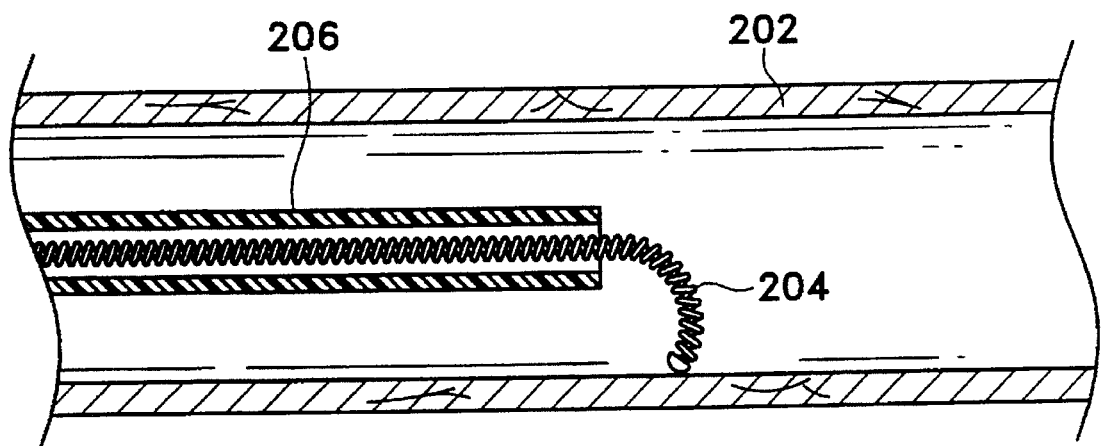
Figure 16C:
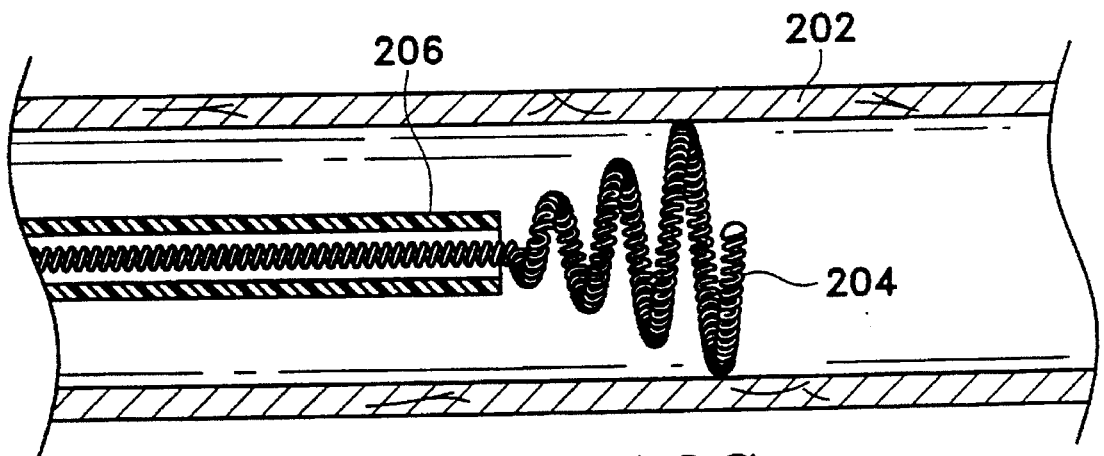

FIGS. 16A, 16B, and 16C depict a common deployment method for the inventive vasoocclusive device as described here. It may be observed that these procedures are not significantly different than those described in Ritchart et al. (U.S. Pat. No. 4,994,069). During the period the inventive vasoocclusive device is situated within the constraining tubular member making up the catheter, the vasoocclusive device maintains its primary form, which clearly is generally linear or at least is within the constraining catheter lumen. As the helically wound primary tubular member exits the constraining catheter, the helically wound tubular member assumes a secondary configuration, different from the first configuration, which secondary configurations have been shown and discussed with relation to the figures above. The major difference in the procedure is the propensity of the device as described here to engage the wall of the vessel lumen as it exits the catheter distal tip.

FIG. 16A shows the distal tip of the catheter (200) which is within the lumen of an artery (202). The distal or end section (204) of the coil is shown emerging from the distal dip of the catheter (200). The distal end portion (204) is shown beginning to droop towards the wall of the blood vessel (202).

In FIG. 16B, the end section (204) has proceeded farther out of the catheter distal end (206) and has engaged the wall of the blood vessel (202). In FIG. 16C, the end section (204) is along the wall of the vessel (202) and the secondary shape of the vasoocclusive device is beginning to form. As the vasoocclusive device continues to extend from the catheter (206) it will become more conical in shape and will form an occlusive site within vessel (202)

Not shown in the drawings are a variety of deployment tips suitable for assisting in deployment of the inventive vasoocclusive device. In one such variation, the deployment tips are electrolytically decomposable regions. Such a concept and details of any structure may be found in U.S. Pat. Nos. 5,122,136 and 5,354,295, to Guglielmi and Sepetka. Severally, the deployment tips may be mechanical in nature. Such connective joints are shown in a variety of patents assigned to Target Therapeutics, Inc., of Fremont, Calif. Such patents include U.S. Pat. No. 5,234,437, to Sepetka; U.S. Pat. No. 5,250,071, to Palermo; U.S. Pat. No. 5,261,916 to Engelson; U.S. Pat. No. 5,304,195, to Twyford et al.; U.S. Pat. No. 5,314,415, to Palermo; and U.S. Pat. No. 5,350,397, to Palermo et al. None of these detachment devices are critical to this invention.

Modification of the above-described variations of carrying out the invention would be apparent to those of skill in the fields of medical device design generally, and vasoocclusive devices, specifically, and such variations are intended to be within the scope of the following claims.

We claim as our invention:

1. A vasoocclusive device comprising:
    an elongated wire helically wound into a tubular member having a first end, a second end, an axis extending between said first and second ends, and wherein the helically wound tubular member has a first configuration conforming to a lumen within a constraining tubular member when constrained within that constraining tubular member, and wherein the helically wound tubular member has a second self-forming secondary configuration, different from the first configuration, when not constrained by the constraining tubular member, and wherein the helically wound tubular member has at least one region of flexibility which is more highly flexible than at least one region adjacent said at least one region of higher flexibility, and wherein the secondary configuration is generally conical in shape.

2. The vasoocclusive device of claim 1 wherein the elongated wire in the at least one region of higher flexibility is more flexible than is the wire in another region of the helically wound tubular member.

3. The vasoocclusive device of claim 1 wherein the diameter of the helically wound tubular member in the region of higher flexibility is smaller than another region of helically wound tubular member.

4. The vasoocclusive device of claim 1 wherein the at least one region of higher flexibility has a helical pitch spacing rendering the region more flexible than another region in said helically wound tubular member.

5. The vasoocclusive device of claim 1 additionally comprising filamentary material attached to said helically wound tubular member.

6. The vasoocclusive device of claim 1 additionally comprising a deployment tip attached to at least one of the first end and second end.

7. The vasoocclusive device of claim 6 wherein the deployment tip comprises a mechanically detachable end adapted to attach to and detach from a pusher.

8. The vasoocclusive device of claim 6 wherein the deployment tip comprises an electrolytically detachable end adapted to detach from a pusher by imposition of an electrical current on said pusher.

9. The vasoocclusive device of claim 1 additionally comprising a cap on at least one of the first end and second end.

10. A vasoocclusive device comprising an elongated wire helically wound onto a tubular member having a first end, a second end, a primary axis extending between said first end and second end, wherein the helically wound tubular member has a configuration conforming to a constraining tubular member when constrained within said constraining tubular member, and wherein the helically wound tubular member has a second self-forming secondary configuration, different from the first configuration, when not constrained by the constraining tubular member, and wherein the secondary configuration has an axis and a generally conical shape when viewed perpendicular to that axis and wherein said conical shape comprises a series of connected generally straight regions when viewed in line with said axis.

11. The vasoocclusive device of claim 10 wherein the helically wound tubular member has at least one region of flexibility which is more highly flexible than at least one region adjacent said at least one region of higher flexibility.

12. The vasoocclusive device of claim 11 wherein the elongated wire in the at least one region of higher flexibility is more flexible than is the wire in another region of the helically wound tubular member.

13. The vasoocclusive device of claim 11 wherein the diameter of the helically wound tubular member in the region of higher flexibility is smaller than another region of helically wound tubular member.

14. The vasoocclusive device of claim 11 wherein the at least one region of higher flexibility has a helical pitch spacing rendering it yet flexible than another region in said helically wound tubular member.

15. The vasoocclusive device of claim 10 additionally comprising filamentary material attached to said helically wound tubular member.

16. The vasoocclusive device of claim 10 additionally comprising a deployment tip attached to at least one of the first end and second end.

17. The vasoocclusive device of claim 16 wherein the deployment tip comprises a mechanically detachable end adapted to attach to and detach from a pusher.

18. The vasoocclusive device of claim 16 wherein the deployment tip comprises an electrolytically detachable end adapted to detach from a pusher by imposition of an electrical current on said pusher.

19. The vasoocclusive device of claim 10 additionally comprising a cap on at least one of the first end and second end.

20. A vasoocclusive device comprising an elongated wire helically wound onto a tubular member having a first end, a second end, a primary axis extending between said first end and second end, wherein the helically wound tubular member has a configuration conforming to a constraining tubular member when constrained within said constraining tubular member, and wherein the helically wound tubular member has a second self-forming secondary configuration, different from the first configuration, when not constrained by the constraining tubular member, and wherein said secondary configuration comprises a first conical section having an axis and a second filler section.

21. The vasoocclusive device of claim 20 wherein the filler section is generally cylindrical and has an axis, which axis is generally parallel to the axis of the first conical section.

22. The vasoocclusive device of claim 20 wherein the filler section comprises a cylinder having an axis generally perpendicular to the axis of the first conical section.

23. The vasoocclusive device of claim 20 wherein the first conical section is approximately elliptical in form when viewed along said axis.

24. The vasoocclusive device of claim 20 additionally comprising filamentary material attached to said helically wound tubular member.

25. The vasoocclusive device of claim 20 additionally comprising a deployment tip attached to at least one of the first end and second end.

26. The vasoocclusive device of claim 25 wherein the deployment tip comprises a mechanically detachable end adapted to attach to and detach from a pusher.

27. The vasoocclusive device of claim 25 wherein the deployment tip comprises an electrolytically detachable end adapted to detach from a pusher by imposition of a current on said pusher.

28. The vasoocclusive device of claim 20 additionally comprising a cap on at least one of the first end and second end.

* * * * *

UNITED STATES PATENT AND TRADEMARK OFFICE

CERTIFICATE OF CORRECTION

PATENT NO. : 5,649,949

DATED : July 22, 1997

INVENTOR(S) : Michael P. Wallace et al.

It is certified that error appears in the above-identified patent and that said Letters Patent is hereby corrected as shown below:

*column 1, line 66*: change "Richart et al." to -- Richart et al. --. (2nd occurrence).

*column 3, line 42*: change "tureen." to -- lumen.--.

*column 5, line 2*: change "mm" to --turn--.

*column 5, line 10*: change "rams" to --turn--.

*column 5, line 12*: change "rams" to --turns.--.

Signed and Sealed this

Twenty-eighth Day of October, 1997

Attest:

BRUCE LEHMAN

*Attesting Officer*   *Commissioner of Patents and Trademarks*